Figure 1:
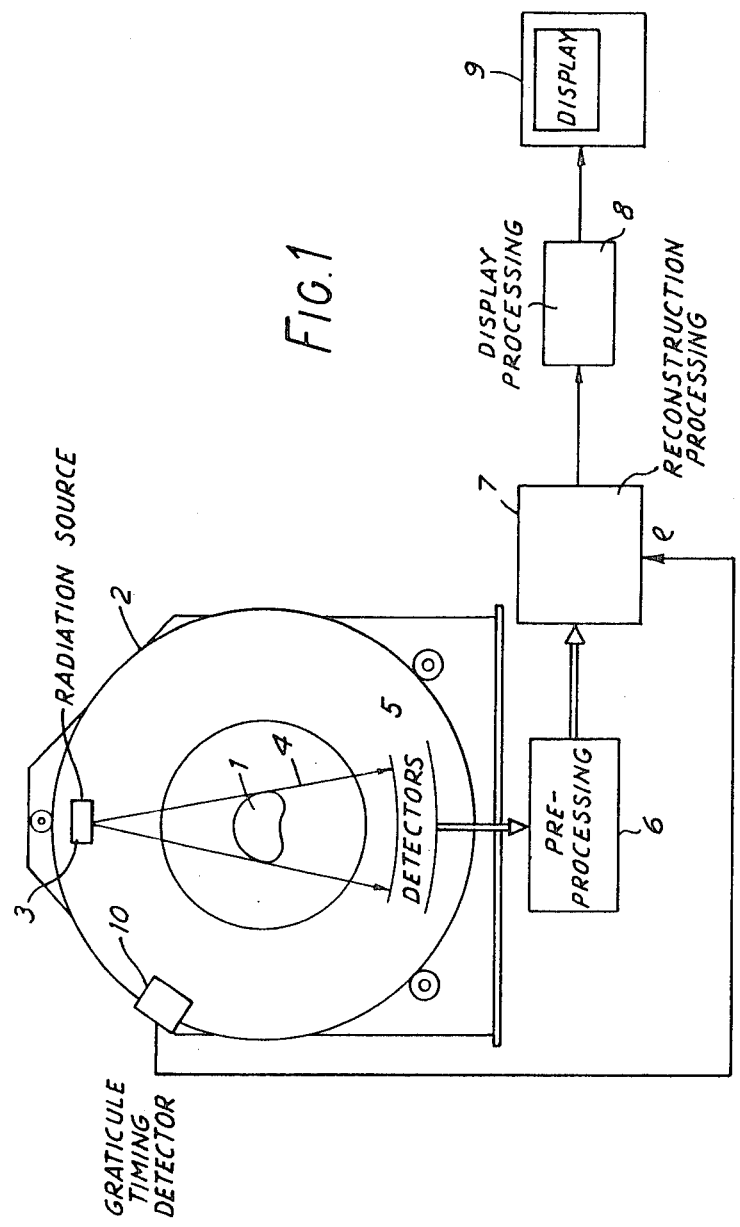

United States Patent [19]

Moore

[11] 4,222,104
[45] Sep. 9, 1980

[54] RADIOGRAPHY

[75] Inventor: John F. Moore, Lake Bluff, Ill.

[73] Assignee: E M I Limited, Hayes, England

[21] Appl. No.: 957,101

[22] Filed: Nov. 2, 1978

[51] Int. Cl.² .................... A61B 6/02; G06F 15/52
[52] U.S. Cl. ............................... 364/414; 364/527;
364/515; 250/445 T
[58] Field of Search ................. 364/414, 527, 515;
250/362, 363 R, 369, 359, 445 T

[56] References Cited

U.S. PATENT DOCUMENTS

| | | | |
|---|---|---|---|
| 3,778,614 | 12/1973 | Hounsfield | 250/366 X |
| 3,924,129 | 12/1975 | LeMay | 250/336 |
| 4,002,910 | 1/1977 | LeMay | 250/445 T X |
| 4,088,887 | 5/1978 | LeMay | 250/445 T X |
| 4,118,628 | 10/1978 | Hounsfield | 250/445 T |
| 4,135,095 | 1/1979 | Watanabe | 250/445 T |
| 4,135,247 | 1/1979 | Gordon et al. | 250/445 T X |
| 4,149,081 | 4/1979 | Seppi | 364/515 X |
| 4,149,249 | 4/1979 | Pavkovich | 364/414 |
| 4,149,250 | 4/1979 | Jass | 364/414 |
| 4,149,259 | 4/1979 | Kowalski | 364/724 |

Primary Examiner—Edward J. Wise
Attorney, Agent, or Firm—Cooper, Dunham, Clark, Griffin & Moran

[57] ABSTRACT

In a CT scanner attenuation data are determined for a plurality of sets of radiation paths through a body and a representation of the distribution of attenuation in the body is obtained from them. It is known to recompute attenuation data for such paths from a first estimate of the representation to take account of heavily attenuating regions which cause errors due to, for example, changes of radiation hardness therein and to then recompute a corrected representation. Conventionally the original data are for sets of parallel beams and the recomputation (or second pass) is performed for parallel paths using the same algorithm, i.e. the same procedure of modifying electrical signals by electronic circuits specially constructed and configured to carry out the desired procedure. The original data can be for fan distributed sets of paths and processed in that form. Then the second pass, using the same algorithm, is for fan distributed paths. This invention proposes to achieve the first processing to the first estimate using a procedure and electronic circuits for fan distributed paths and to achieve the second pass using the algorithm a procedure and circuits for parallel paths.

7 Claims, 6 Drawing Figures

RADIOGRAPHY

The present invention relates to medical radiographic apparatus of the type known as computerised tomographic (CT) scanners.

In CT scanners, such as that described in U.S. Pat. No. 3,778,614, penetrating radiation, for example X-radiation, travels in a slice of the body of a patient to be examined. A source of the radiation orbits about the patient and projects the radiation in a plurality of different directions angularly distributed in the slice. The intensity of radiation emerging from the slice is then measured along each of a plurality of narrow beam paths. For the purpose of examining the patient, at least a part of the slice is designated as a matrix of elemental areas, for each of which an estimate of the attenuation of the radiation therein is to be obtained. The narrow beam paths are distributed so that each elemental area is intersected by a suitably large number of them. The intensity measurement obtained for each path is then representative of the total attenuation suffered by the radiation in passing through all of the elemental areas intersected by the path. The path, in practice, intersects only part of some elemental areas and due allowance is made for this.

The intensity measurements are then processed, for example as described in the said United States Patent, or in U.S. Pat. No. 3,924,129, to generate a picture in which each point has a brightness corresponding to the absorption of radiation in the corresponding positioned elemental area of the region. The disclosures of the said Patents are hereby incorporated herein by reference.

One source of error in this process results from the fact that absorption is not uniform for radiation of different energies. Thus low energy radiation is preferentially absorbed leading to "hardening" of the radiation. For tissue having relatively low absorption this effect may not be significant. However, for high absorption material, such as bone, the hardening is significant, leading to erroneous intensity measurements for other elemental areas as the respective paths.

Another source of error results from scattering of the radiation. This attenuation error is, like attenuation by absorption, related to the density of the tissue through which the radiation passes.

To correct for these and similar errors which are related to the tissue density, it is necessary to have some knowledge of the tissue density distribution, which is of course provided by the finally derived representation. It has been proposed to evaluate a first estimate of this representation, which will include the errors mentioned. This gives some, although not totally correct, knowledge of the tissue density distribution. The representation is then used to recalculate total attenuation measurements for paths through the body, these being similar to those first measured by the detector means. This is achieved by methods for summing attenuation along a beam path, such as those described in U.S. Pat. No. 3,778,614. The recalculated attenuation measurements are processed to take account of errors such as hardness and scattering errors and used to form a corrected representation.

It is an object of the invention to provide an improved procedure for forming and reforming the representation, the procedure being applicable to different forms of processing and error correction as desired.

It is another object of the invention to provide a method of processing sets of data signals each representing the attenuation of radiation along individual beam paths, angularly spaced in one of a plurality of fan-shaped distributions of beam paths directed through the body of a patient, to provide a representation of the distribution of attenuation of the radiation in a slice of the body, the method including the steps of: (a) modifying the data signals by combination with weighted contributions from other signals of the same set and interpolating between the modified data signals to provide data signals relating to a larger number of paths angularly spaced in the fan-shaped distribution; (b) back projecting the original and interpolated data signals onto elements of a matrix of elements notionally defined in said slice; (c) forward projecting from said matrix along a plurality of sets of parallel paths notionally defined in said slice to provide attenuation data for those notional paths; (d) correcting the attenuation data for the notional paths for errors relating to the distribution of attenuation in different parts of the slice; and (e) back projecting the corrected attenuation data along said parallel paths onto said matrix to provide a representation of said distribution of attenuation which is at least in part corrected for said errors.

Figure 2:
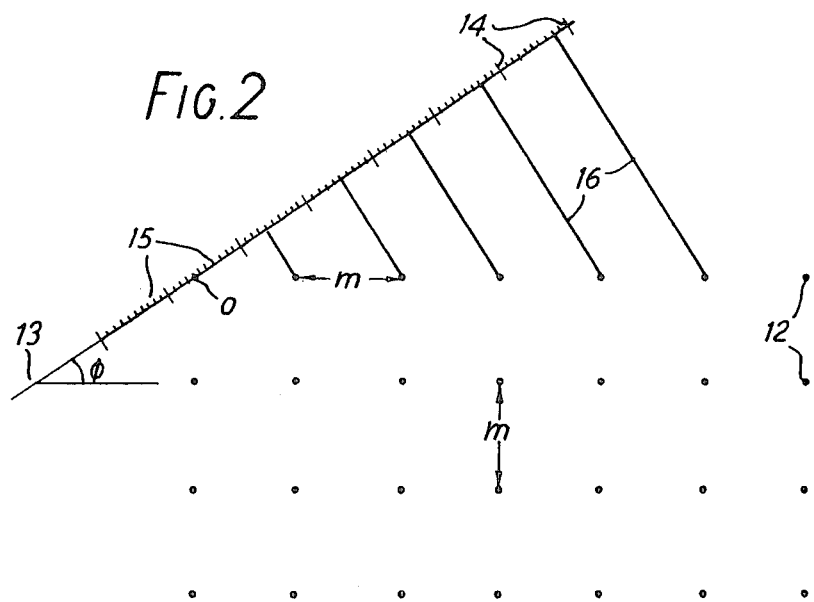
Figure 4:
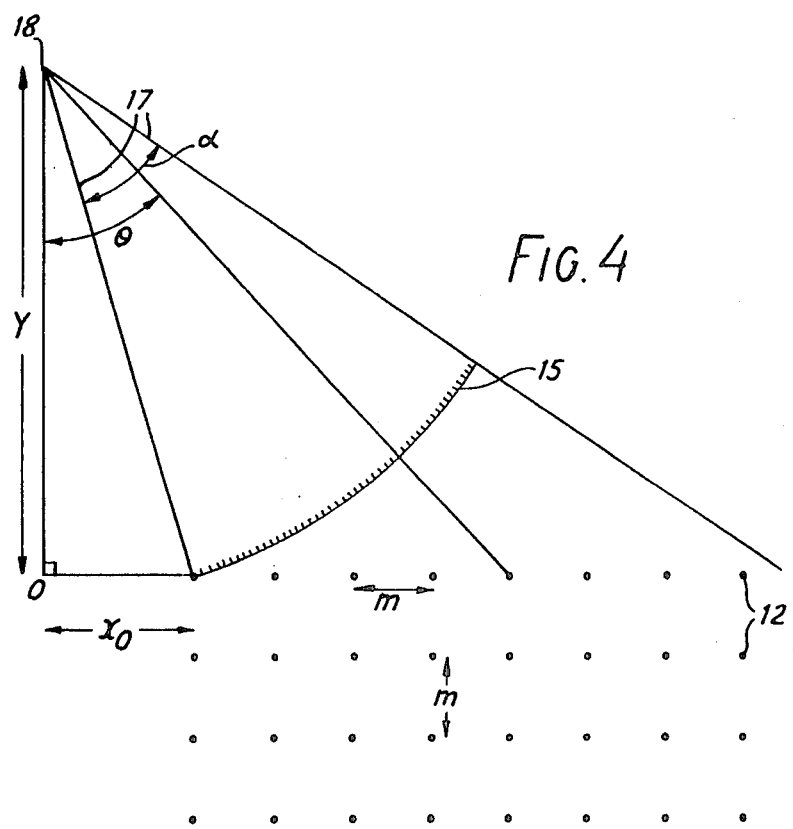
Figure 3:
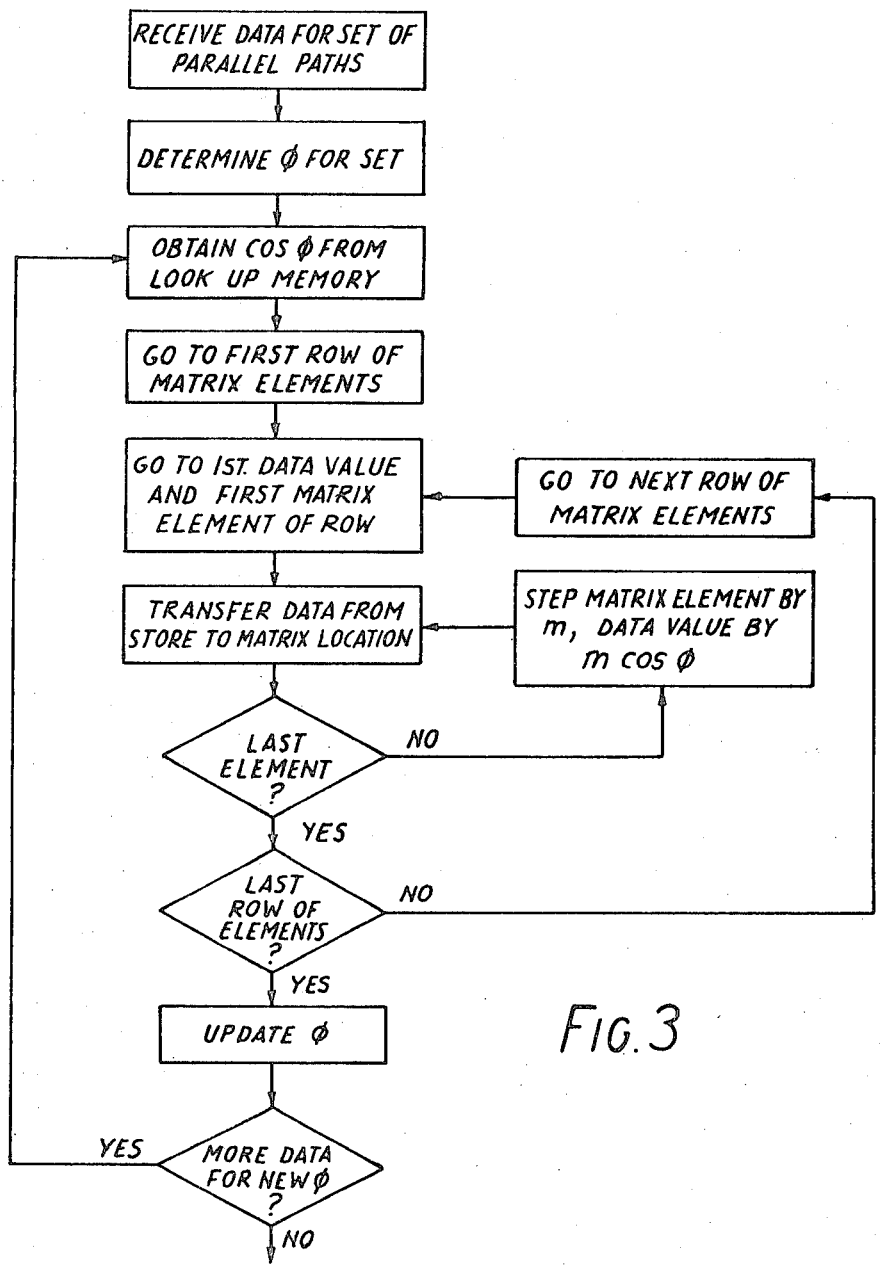
Figure 5:
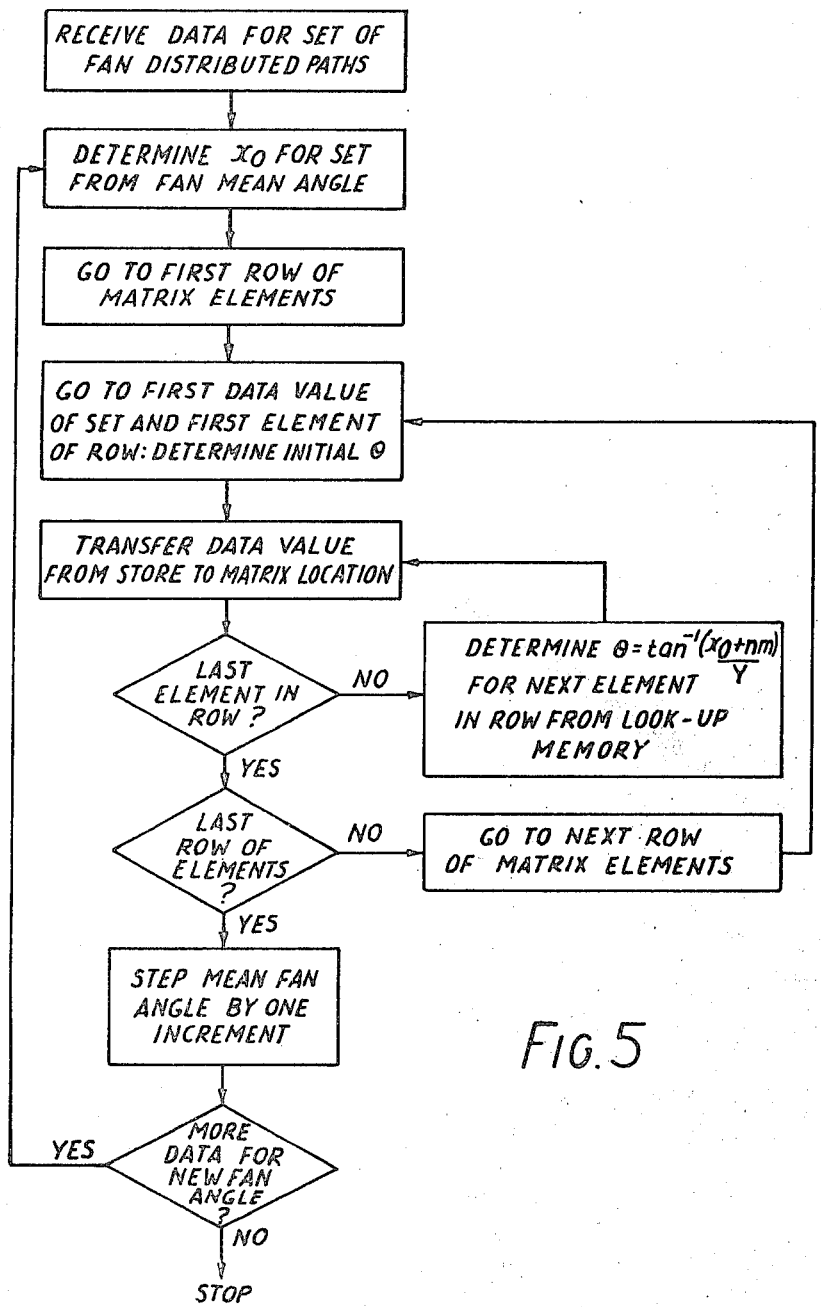
Figure 6:
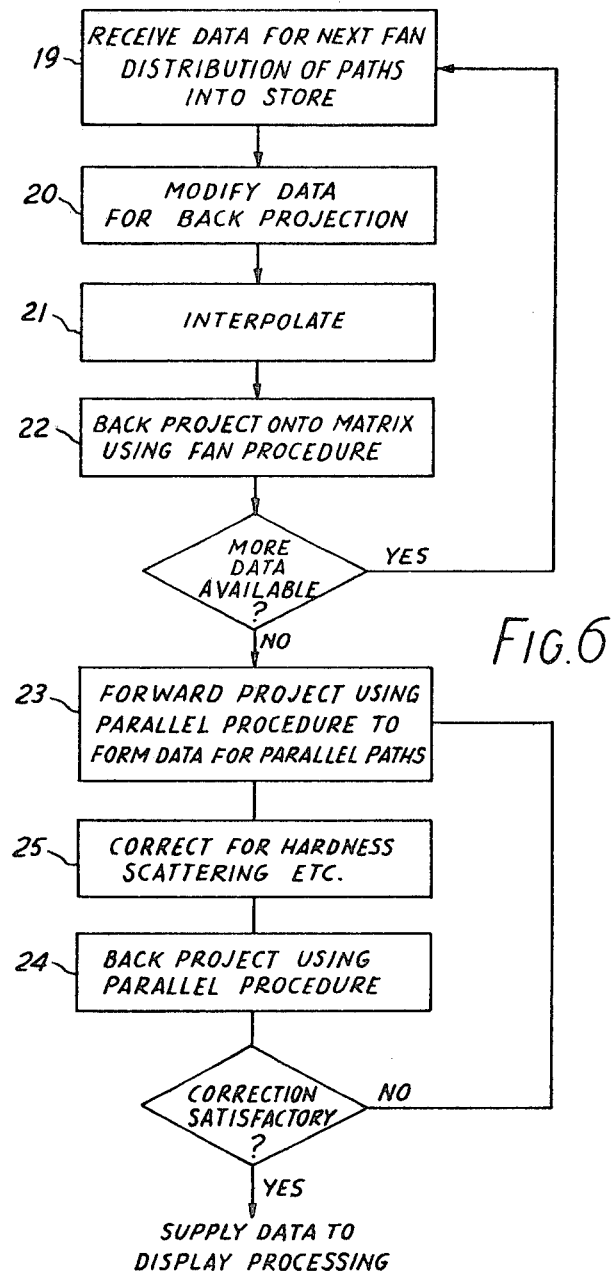

In order that the invention may be clearly understood and readily be carried into effect, it will now be described by way of example with reference to the accompanying drawings of which, FIG. 1 shows in simplified form a CT apparatus with which the invention may be used, FIG. 2 is used to explain the back projection of data for parallel paths through the body, FIG. 3 is a flow diagram for the back projection of FIG. 2, FIG. 4 is used to explain the back projection of data for paths angularly distributed in the body, FIG. 5 is a flow diagram for the back projection of FIG. 4, and FIG. 6 is a flow diagram for the method of the invention, including the procedures of FIGS. 2 and 3, and FIGS. 4 and 5.

FIG. 1 shows in diagrammatic form one type of CT apparatus with which this invention can be used. Data, relating to the attenuation of radiation in a body 1, are obtained in a scanning apparatus indicated generally. The scanning part is mounted on a rotating member 2 and includes a radiation source 3, directing a fan distribution of radiation 4 through body 1, and detectors 5 receiving the radiation. The example illustrated is essentially that described in U.S. Pat. No. 4,035,647 in which the source and detectors are orbited around the body. In the course of the rotation the outputs of the detectors are repeatedly sampled. Each sampling gives, from the detectors, output signals representing radiation received along respective ones of a set of angularly distributed paths in the fan distribution. The different samples then provide data for many such sets of paths each at a different mean angle in the slice. The invention may be used with other forms of apparatus, for example one in which a large number of detectors do not rotate and the radiation moves across them.

The data are preprocessed by circuits 6 in which they are converted to digital and logarithmic form and any other operations required. These data signals therefore represent measurements of the attenuation of the radiation along the respective paths. The data signals are then processed in circuits 7 to provide the desired reconstruction of the distribution of attenuation in the examined slice. They represent attenuation values of elements of the matrix referred to hereinbefore and each datum is entered into store at a location corresponding to the respective element. They are further subjected to display processing in circuits 8 to be provided in a form compatible with a chosen display 9. This invention is, however, concerned with a part of the processing included in circuits 7 and the subsequent display processing will not be further described. Circuits 7 require information indicative of the progress of the scanning so that each data signal may be correctly identified with a particular radiation path. For this reason the apparatus includes a graticule timing detector 10. In this example the detector comprises opaque markings on a transparent substrate co-operating with a photocell unit which detects interruption, by the markings, of light from a source included therein, to provide pulses indicative of the rotation of source 3. The graticule may alternatively be reflective or other motion detectors, such as a magnetic pick-up or a separate geared shaft encoder may be provided.

It has been mentioned that the processing can be based on the convolution method described and claimed in U.S. Pat. No. 3,924,129.

In that method the detector output signals are arranged in sets corresponding to sets of paths through the body. The output signal for each path is modified by the combination of other output signals in the same set in a procedure clearly explained therein.

The desired representation is formed by adding into a storage location for each matrix element the modified signals for all paths passing through that element and the modification procedure is in fact arranged to make this possible. This addition is effected by taking each beam and adding its modified signal to all elements along the corresponding path. Of course, not all paths totally intercept all elements there along and the signals are weighted to account for the production of interception. Alternatively, this interpolation can be achieved by providing interpolated signals for paths which do substantially intercept a particular element.

The procedure of adding the signals into locations for matrix elements is called "back projection" and is now well established, being described first in the said U.S. Pat. No. 3,778,614. The back projection procedure first applied provides a representation which, as explained hereinbefore may be incorrect because of hardness error, scattering errors, etc. A correction can be made in a so-called "second pass". The data signals for paths through the matrix are reconstituted by the reverse of back projection, appropriately called "forward projection". This simply requires summing, for each path, the absorption values for all elements along that path and is also a procedure described in U.S. Pat. No. 3,778,614. They are then corrected to take account of the errors to be considered and the corrected signals once more back projected to form a corrected representation. The procedure of forward projection, correction and back projection may be repeated to give a more accurate representation if desired.

The corrections may be achieved by performing the forward projection only on attenuation values above a threshold thus calculating corrections which on back projection are added to the first estimated representation. That is, in effect, the first reconstruction is used to indicate those areas of the body giving rise to largest errors. One example of such a correction procedure is described in co-pending U.S. Patent Application Ser. No. 811,281. However it is emphasized that the nature of the corrections to be performed is not a part of this invention and may take any suitable form. This invention is concerned with an improvement of the back projection, forward projection, back projection sequence.

One form of CT apparatus, which has proved to be successful in medical use, provides data signals for sets of paths in which all of the paths of a set are parallel to each other. When modified and interpolated the signals are therefore back projected along the parallel paths into the matrix. For the second pass they are forward projected along parallel paths, corrected and once more back projected along the parallel paths. The procedure is simple to perform since an address selector routes the signals and clocks from one element to the next and from one path to the next in straightforward manner facilitated by the uniform spacing of parallel paths.

FIG. 2 illustrates the procedures followed in back projection of sets of data for parallel beams. It is emphasized that the procedure is well established and commonly used, although not necessarily in the form described here. In FIG. 2 there is shown part of a Cartesian matrix of elemental areas in the region of the body 1 being examined. Each element is considered to be a solid element with rectangular sides and is denoted by its centre point 12. Each point 12 corresponds to a storage location in a data store in which the representation is to be assembled and the data are to be organised in the data store in a manner simulating the procedures to be described.

The matrix elements are spaced by a separation m and are interselected by beams of radiation whose paths are parallel and perpendicular to the line 13. Although the paths are of finite width, their data values are considered to be for their centre lines, which cross lines 13 at points 14. This does not, in practice, provide sufficient beams to pass through all matrix elements 12 and therefore the data values for the paths are interpolated to provide an increased number of data values which could have been measured for paths whose centre lines cross lines 13 at points 15. As mentioned, many such sets of paths cross body 1 at many different orientations. That illustrated is considered to be inclined to the rows of matrix elements at an arbitary angle $\phi$.

The back projection procedure requires that for each storage location there are summed the modified attenuation value, real or interpolated, for all paths, one for each set, the centre line of which passes through the corresponding matrix element. The data signals can be allocated to the matrix elements in any order. However, it is desirable to use a sequence which is efficient in data organisation. It is therefore usual to back project at one time into a well defined group of storage locations, which may typically be a row, column or diagonal of the matrix of elements. For example, each element of the upper row in FIG. 2 receives, from the set of data values shown, a value for a beam indicated by a line 16. (The first point lies on line 13).

This result is achieved by holding the interpolated data signals in storage and counting through the stored values for the set from an arbitary starting point, simultaneously counting along the matrix elements from one location to another. If the counting is set to start from an origin O at the first location 12, the matrix addresses are counted by the circuits in equal increments of steps of m units and this will be the same for each matrix row or column. To keep step the interpolated value store addresses must step through equal increments 16 of m Cos φ. Cos φ changes when a new set of paths is selected but is constant for counting along one set. At each step the corresponding data value is transferred from the current address in one store to the current address in the other.

FIG. 3 shows a flow diagram illustrating the sequence of steps described hereinbefore for back projection of data for a number of sets of parallel paths at different angles φ onto rows of matrix elements. The diagram is self-explanatory in the light of the preceding explanation and will not be further explained. The procedure for forward projection of parallel data can be the reverse of that described. Alternatively, the data can be summed for individual beams.

Alternative forms of CT apparatus acquire the original data as sets of signals relating to sets of paths of which the paths of each set are distributed in a fan originating at a focus. The focus may be the source of the radiation, which spreads in a fan or may be a notional focus defined by the particular form of scanning used. One procedure which can be adopted to process these fan distributed sets of signals is to reorganise them into data for sets of parallel paths, which can readily be achieved if suitable steps are taken in the scanning. In that event the back projection and second pass are both performed for parallel paths and are identical to those described hereinbefore. Such an arrangement is, however, subject to disadvantages, one of which is that the reorganisation into parallel sets is further processing and increases the total processing time.

An alternative procedure which can be adopted is to process the data using a development of the said convolution processing which is suitable for sets of data for fan distributed paths. Suitable modifications have been described, for example, in U.S. Pat. No. 4,088,887, and the theory of such modifications has been described by Hermans, Lakshminarayanan and Narparstek "Reconstruction using divergent-ray shadowgraphs" from "Reconstruction tomography in diagnostic radiology and nuclear medicine" ed. Ter-Pogossian et. al. pp. 105-117, 1977, University Park Press, Baltimore, and others.

If such an alternative procedure is adopted, the back projection is also along the fan distributed paths. This does not resent any problem since the positions of the paths and the elements of the matrix are known in advance; thus an address selector can be clocked to move from one matrix element to another along the paths and between paths.

FIG. 4 shows part of the same matrix of elements 12 as in FIG. 2 intercepted by a fan distribution of paths. The paths are considered to extend between limits 17 over an angle α from a focus 12, which may be the radiation source. The modified data for irradiated beam paths have been interpolated and the increased number of paths, for which data are thus available, are shown by the points 15 at which they cross an arc about 18. As for as the parallel path case, the data for these interpolated paths are held in a store and it is desired to transfer them to the locations for the elements in the matrix store, such that each element receives the data value for the path which comes closest to passing through its centre point 12.

The procedure for this back projection is essentially the same as described in relation to FIG. 2 but, for equal steps of address along the matrix row, the interpolated store address is stepped by different increments related to angle φ, which is the angle of inclination of an individual path to the matrix columns. It will be seen that, from origin O, each successive step along the matrix row requires a greater step along paths 15. If the addresses in the store for interpolated data are identified by values φ, which is convenient, then for a matrix element $x_0 + nm$ from O the correct interpolated data value to be selected and applied to the corresponding matrix storage location is determined by $$\theta = \tan^{-1}\left[\frac{(x_o + nm)}{Y}\right]$$

from O. This can be determined with the aid of a memory arranged as a look-up table but the arctangent memory must be accessed for each step.

A flow diagram similar to that of FIG. 5, but for the fan back projection, is shown in FIG. 5. Forward projection is similar. It will be seen that the procedure will be more lengthy than that of FIG. 3, at least because a calculation of $(x_o+nm)/Y$ and determination of its arctangent from look-up table memory is included in the inner of three loops, where it must be carried out for each new matrix location. In contrast the parallel set case of FIG. 2 includes the determination of Cos φ from look-up table memory, but this is in the outer loop and need only be carried out once for each set of paths. It is nevertheless still advantageous to accept the increased back projection time in return for the other benefits of processing the data for fan distribution paths.

However, because of the inherently non-uniform nature of these divergent paths, the back projection procedure is necessarily more lengthy than that for parallel paths. It is nevertheless still advantageous to accept this increased back projection time in return for the benefits of processing the data for fan distributed paths.

Conventionally, therefore, the system is arranged to back project then forward project (for correction purposes) and back project again along the fan distributed paths.

This invention proposes that it is not necessary to perform all of the back projection and the second pass along the same paths. The first back projection of the modified data must be for the fan distributed paths for which they were originally measured (including paths interpolated therebetween), if the data are not to be re-arranged. However, the second pass, while it should use the same paths for both forward and back projection, need not be for the paths irradiated. It can be for any paths which have a substantially uniform distribution across the matrix. It is therefore proposed that the second pass be performed for sets of parallel paths, of substantially uniform distribution, in which case the relatively shorter time in which a parallel path back or forward projection can be performed shortens the total processing time. The processing can be further speeded by using less sets of paths or less paths in each set or both for the second pass since it is used only for correction, of an already determined representation, which can use data of reduced spatial frequency.

There is shown in FIG. 6 a flow diagram of the procedure to be followed to implement the invention. The data, which are taken into storage at 19 are modified at 20 by a procedure which may be essentially that described in U.S. Pat. No. 3,924,129, but which will be modified as discussed hereinbefore for processing of data for radiation paths in a fan distribution. The modification may take any other known form if desired. The data are then interpolated at 21 to provide data for an increased number of paths so that one will pass sufficiently close to each matrix element. A particularly beneficial and suitable form of interpolation is that described in U.S. Pat. No. 4,002,910.

The first back projection step shown at 22 is one for a fan distribution of paths and may be as explained with reference to FIGS. 4 and 5 but may take other forms.

The forward projection at 23 and second back projection 24 are, in accordance with this invention, a procedure using parallel radiation paths. This may be as explained with reference to FIGS. 2 and 3. However, it will be remembered that the forward and back projection of data for parallel beam paths is now a well established procedure, having been described in U.S. Pat. No. 3,778,614, and many variations are known.

It is emphasized that the improvement provided by this invention does not depend on the particular procedures chosen either for fan distribution or parallel distribution projection. The invention results from the realization that it is not necessary for the forward and second back projections to relate to the beam paths irradiated or to the first back projection, that they need not therefore use the same procedure as the first back projection and that, notwithstanding the need to provide extra hardware or an extra algorithm for a computer, the gain in processing time justifies a mixed procedure.

It should be noted that the step 25 shown, for providing hardness variation, scattering and other corrections, provides the reason for the steps 23 and 24 to which the invention is an improvement. The invention is, however, applicable to any steps such as 25 which require forward projection and is not restricted to and does not rely on the actual examples given.

FIG. 6 includes a recirculating loop to correct until a satisfactory result is obtained. That is not necessary if not desired since a fixed number of corrections, including one only, may suffice.

The procedures shown herein as flow diagrams may conveniently be implemented by specially designed circuits. However, the CT apparatus with which they will be used conventionally includes a special purpose or suitably programmed general purpose digital computer. Since the procedures in the main involve transfer of data one form of storage to another, with appropriate procedures for address selection to re-arrange and combine them, it is convenient and straightforward to program the same computer to simulate the steps of the flow diagrams.

Other arrangements to implement this processing including the variation will readily be apparent to those with the appropriate skills.

What we claim is:

1. A method of processing sets of data signals each representing the attenuation of radiation along individual angularly spaced beam paths of a corresponding one of a plurality of fan-shaped distributions of beam paths directed through the body of a patient, to provide a representation of the distribution of attenuation of the radiation in a slice of a body, the method including the steps of: (a) modifying the data signals by combination with weighted contributions from other signals of the same set; (b) distributing from each set, to each element of a matrix of elements notionally defined in the said slice, one modified data signal, relating to one of said fan distribution of paths which intersects said element or a value interpolated between the modified data signals to relate to a notional path which intersects that element to form a first estimate of said representation; (c) deriving, from said first estimate, notional data values representing the attenuation which would be suffered in a body having the estimated attenuation distribution along paths of a plurality of paths of each of a plurality of sets of parallel paths through the distribution; (d) correcting said notional data values for errors relating to the different distribution of attenuation in different parts of the body through which the radiation has passed; and (e) redistributing the corrected notional data values of the elements of the said matrix to provide a further estimate of said representation corrected for said errors.

2. A method according to claim 1 including repeating the steps of deriving notional data values, correcting and redistributing to further correct said representation.

3. A method of processing sets of data signals each representing the attenuation of radiation along individual beam paths angularly spaced in one of a plurality of fan-shaped distributions of beam paths directed through the body of a patient, to provide a representation of the distribution of attenuation of the radiation in a slice of the body, the method including the steps of: (a) modifying the data signals by combination with weighted contributions from other signals of the same set and interpolating between the modified data signals to provide data signals relating to a larger number of paths angularly spaced in the fan-shaped distribution; (b) back projecting the original interpolated data signals onto elements of a matrix of elements notionally defined in said slice; (c) forward projecting from said matrix along a plurality of sets of parallel paths notionally defined in said slice to provide attenuation data for those notional paths; (d) correcting the attenuation data for the notional paths for errors relating to the distribution of attenuation in different parts of the slice; and (e) back projecting the corrected attenuation data along said parallel paths onto said matrix to provide a representation of said distribution of attenuation which is at least in part corrected for said errors.

4. A method according to any one of claims 1, 2, or 3 in which said errors include errors caused by variations of hardness induced in the radiation transmitted along the beam paths.

5. A method according to any one of claims 1, 2, or 3 in which said errors include errors caused by scattering of said radiation, from said beam paths, by material of said body.

6. A method according to any one of claims 1, 2, or 3 in which steps (c) and (e) are carried out using a smaller number of paths in each parallel set then were used in the fan-distributed sets of paths in step (b).

7. Apparatus for examining a body slice by means of penetrating radiation such as x-radiation, the apparatus including a scanning arrangement having means for projecting the radiation through the body slice and means for detecting the intensity of the radiation after passage through the body and for providing sets of data signals where each set represents the attenuation of the radiation along individual directions which are at different angles with respect to the body within a fan-shaped distribution of directions and different sets represent the attenuation of the radiation along such individual directions within fan-shaped distributins which are at different mean angles relative to the body; means for modifying the data signals by combination with other data signals of the same set; means for interpolating between the modified data signals to provide data signals relating to a larger number of directions angularly spaced in the respective fan-shaped distribution; storage means having a plurality of storage locations corresponding to elements of a matrix of elements notionally defined in said slice; means for back projecting the original and interpolated data signals onto storage locations corresponding to elements intersected by the respective directions; means for forward projection from the storage locations corresponding to elements intersected by sets of parallel directions defined in said slice, where different sets of such parallel directions are at different angles relative to the body, to provide attenuation data for those parallel directions; means for correcting the attenuation data for the sets of parallel directions for errors relating to the distribution of attenuation in different parts of the slice; and means for back projecting the corrected attenuation data for the sets of parallel directions to storage locations corresponding to elements of the matrix intersected by said sets of parallel directions to provide a representation of the distribution of attentuation in said slice.

* * * * *